(12) United States Patent
Kuypers (10) Patent No.: US 10,028,749 B2
(45) Date of Patent: Jul. 24, 2018

(54) CORD COLLECTION CLAMP

(71) Applicant: Children's Hospital & Research Center Oakland, Oakland, CA (US)

(72) Inventor: Franciscus A. Kuypers, El Cerrito, CA (US)

(73) Assignee: Children's Hospital & Research Center at Oakland, Oakland, CA (US)

( * ) Notice: Subject to any disclaimer, the term of this patent is extended or adjusted under 35 U.S.C. 154(b) by 271 days.

(21) Appl. No.: 14/942,094

(22) Filed: Nov. 16, 2015

(65) Prior Publication Data

US 2017/0135698 A1 May 18, 2017

(51) Int. Cl.
| | |
|---|---|
| *A61M 5/00* | (2006.01) |
| *A61B 17/122* | (2006.01) |
| *A61M 1/00* | (2006.01) |
| *A61B 17/3211* | (2006.01) |
| *A61B 10/02* | (2006.01) |
| *A61M 1/02* | (2006.01) |
| *A61B 5/15* | (2006.01) |
| *A61B 17/3209* | (2006.01) |
| *A61B 17/32* | (2006.01) |
| *A61B 17/42* | (2006.01) |

(52) U.S. Cl.
CPC .......... *A61B 17/122* (2013.01); *A61B 5/1405* (2013.01); *A61B 5/150038* (2013.01); *A61B 10/02* (2013.01); *A61B 17/32* (2013.01); *A61B 17/3209* (2013.01); *A61B 17/3211* (2013.01); *A61M 1/0019* (2013.01); *A61M 1/02* (2013.01); *A61B 17/42* (2013.01); *A61B 2017/1225* (2013.01); *A61B 2017/320064* (2013.01); *A61B 2017/32113* (2013.01); *A61M 2202/0462* (2013.01); *A61M 2210/1466* (2013.01)

(58) Field of Classification Search
CPC ..... A61B 17/122; A61B 5/1405; A61B 10/02; A61B 17/3211; A61B 2017/1225; A61B 2017/320064; A61M 1/0019; A61M 1/02
See application file for complete search history.

(56) References Cited

U.S. PATENT DOCUMENTS

| | | | |
|---|---|---|---|
| 5,520,699 A * | 5/1996 | Hessel | A61B 17/122 600/564 |
| 5,575,796 A | 11/1996 | King et al. | |
| 5,919,176 A | 7/1999 | Kuypers et al. | |
| 5,993,429 A | 11/1999 | Kuypers et al. | |
| 6,059,794 A | 5/2000 | Webb | |
| 6,190,368 B1 | 2/2001 | Kuypers et al. | |
| 6,440,110 B2 | 8/2002 | Kuypers et al. | |
| 2003/0004521 A1 * | 1/2003 | Oriowski | A61B 17/122 606/120 |

* cited by examiner

*Primary Examiner* — Philip R Wiest
(74) *Attorney, Agent, or Firm* — Michael B. Rubin; Bozicevic, Field & Francis LLP (57) ABSTRACT

The present disclosure provides an apparatus, and methods of using same, for collecting blood from an umbilical cord in a sterile environment that includes an umbilical cord retaining assembly and a blood collection assembly rotatably connected to the umbilical cord retaining assembly. A cord cutting blade, which is carried by the blood collection assembly, functions to cut the umbilical cord when the blood collection assembly is rotated relative to the umbilical cord retaining assembly. After the umbilical cord is cut, blood flows by force of gravity into the blood collection region of the blood collection assembly to which a blood collection bag can be interconnected.

14 Claims, 8 Drawing Sheets

CORD COLLECTION CLAMP

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

TECHNICAL FIELD

The present disclosure relates generally to blood collection devices. More particularly, the present disclosure concerns an apparatus and method for collecting blood from an umbilical cord.

INTRODUCTION

A sample of blood taken from a newborn baby's umbilical cord is a rich source of hematopoietic stem cells. Accordingly, cord blood has been used to treat a wide variety of diseases of the blood and immune system. Typically, cord blood is collected from the umbilical cord vein attached to the placenta after the umbilical cord has been detached from the newborn baby. Methods and devices for collection of cord blood are thus of interest.

SUMMARY

By way of brief summary, the present disclosure provides a novel cord collection clamp for collecting blood from an umbilical cord in an aseptic environment that includes an umbilical cord retainer assembly and a blood collection assembly that is rotatably connected to the cord retainer assembly. The cord retainer assembly includes a channel through which the umbilical cord passes and is provided with an outlet that communicates with the collection chamber of the blood collection assembly. The blood collection assembly is rotatably connected to the retainer assembly and uniquely includes a cord cutting blade that is strategically positioned to move from a first position to a second cord cutting position upon rotation of the collection assembly relative to said retainer assembly, thereby cutting the umbilical cord. The present disclosure also provides methods of collecting cord blood, as well as collecting a sample of the umbilical cord, using a device as described herein.

With the foregoing and mind, the present disclosure provides, in one embodiment, a cord collection clamp of the aforementioned character in which, during the umbilical cord cutting operation, the retainer assembly surrounds the umbilical cord and provides a biological seal.

In a further embodiment, the present disclosure provides a cord collection clamp of the class described which is safer to operate than the prior cord cutting devices because the cord cutting blade of the apparatus is better separated from the operator making careless handling less likely to expose a cutting surface to the operator.

In a further embodiment the present disclosure provides a cord collection clamp of the character described in which the retainer assembly includes a first segment overlaying a portion of the blood collection assembly, a second segment hingeably interconnected to the first segment and movable from a first position to a second position overlaying a portion of the blood collection assembly and a third segment hingeably interconnected to the second segment and movable from a first position to a second position overlaying a portion of said first segment and overlaying a portion of the blood collection assembly.

In a further embodiment, the present disclosure provides a cord collection clamp of the type described in the preceding paragraph in which movement of the second segment of the retainer assembly into the second position functions to safely cover the cutting blade of the blood collection assembly in a manner to prevent accidental cutting of the user and further functions to lockably engage the blood collection assembly in a manner to prevent rotation of the assembly relative to the retainer assembly in a manner to expose the operator to the cord cutting blade.

In a further embodiment, the present disclosure provides a cord collection clamp of the class described in the preceding paragraphs in which the blood collection assembly is provided with a locking member that is engaged by the second segment of the retainer assembly in a manner to block rotation of the blood collection assembly relative to the retainer assembly.

In a further embodiment, the present disclosure provides a cord collection clamp as described in the preceding paragraph in which upon movement of the third segment of the retainer assembly into the second position, the third segment functions to act upon the locking member of the blood collection assembly in a manner to move the locking member out of engagement with the second segment of the retainer assembly so as to permit rotation of the blood collection assembly relative to the retainer assembly thereby permitting safe cutting of the umbilical cord.

In a further embodiment, the present disclosure provides a cord collection clamp as described in the preceding paragraph in which continued rotation of the blood collection assembly relative to the retainer assembly will move the locking member into engagement with an aperture provided in the second segment of the retainer assembly so as to thereby block further rotation of the blood collection assembly relative to the retainer assembly thereby disabling the device.

In a further embodiment, the present disclosure provides a cord collection clamp as described in the preceding paragraph in which, upon cutting of the umbilical cord, blood from the umbilical cord will flow freely by force of gravity into the collection chamber of the blood collection assembly.

In a further embodiment, the present disclosure provides a cord collection clamp of the character described in the preceding paragraphs in which the blood collection chamber of the blood collection assembly is substantially closed to the external environment so that the blood from the umbilical cord is collected in a substantially aseptic environment.

In a further embodiment, the present disclosure provides a cord collection clamp of the character described in the preceding paragraphs that is ergonomically superior to the prior cord cutting devices and one that is easier and less expensive to produce than the prior cord cutting devices.

DETAILED DESCRIPTION

Figure 1:
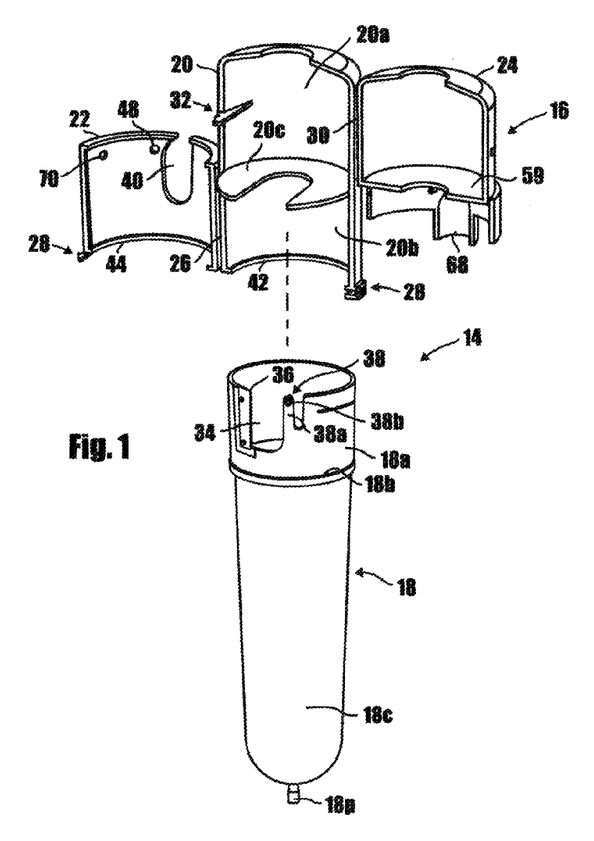
FIG. 1 is an exploded, front elevational view of one form of the cord collection clamp of the present disclosure.
Figure 2:
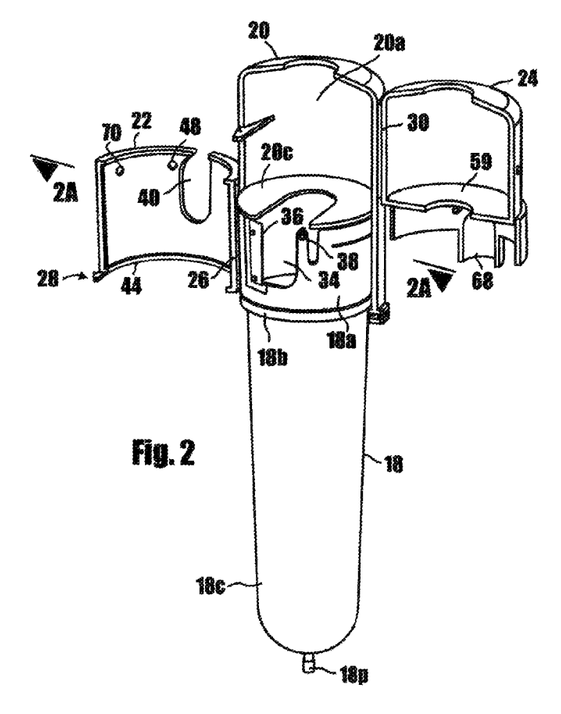
FIG. 2 is a front elevational view similar to FIG. 1, but showing the collection assembly, or lower portion of the cord collection clamp interconnected with the central, or first segment of the retainer assembly of the cord collection clamp.

Referring to the drawings and particularly to FIGS. 1 and 2, one form of the cord collection clamp of the present disclosure for collecting blood from an umbilical cord is there shown and generally designated by the numeral 14. The device here comprises two inter-connectable assemblies, namely an upper, or umbilical cord retainer assembly 16 and a lower, or blood collection assembly 18 that is rotatably connected to the umbilical cord retainer assembly.

Figure 5:
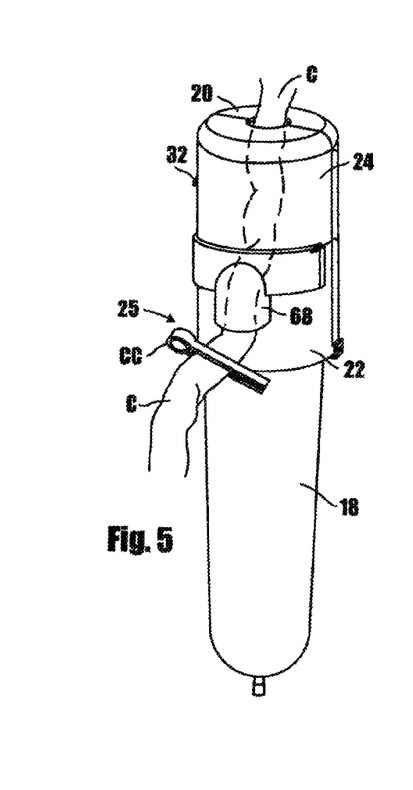
FIG. 5 is a front elevational view similar to FIG. 4, but showing the third segment of the retainer assembly mated with the first segment of the retainer assembly.

The retainer assembly 16 uniquely comprises three hingeably interconnected segments, namely, a first, or central segment 20, a second segment 22 and a third segment 24. In a manner presently to be described, segments 20, 22 and 24 cooperate to form the device housing 25 (FIG. 5). As best seen by referring to FIG. 1 of the drawings, the first segment 20 has an upper portion 20a, a lower portion 20b and includes an intermediate partition wall 20c that divides the upper and lower portions. As depicted in FIG. 2 of the drawings, in using the device of the present disclosure, the upper portion 18a of the collection assembly seats within the lower portion 20b of first segment 20.

Figure 2A:
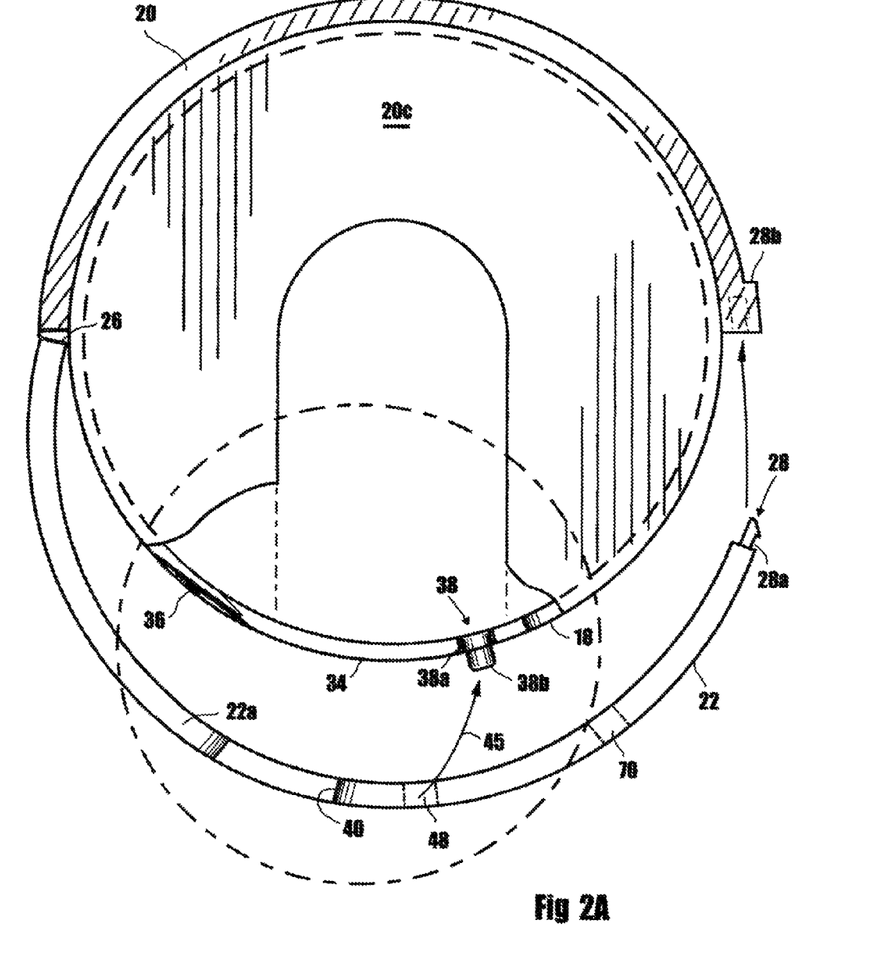
FIG. 2A is a cross-sectional view of the first segment of the retainer assembly taken along lines 2A-2A of FIG. 2 and showing the second segment of the retainer assembly rotated toward a closed position and further illustrating one form of the locking mechanism of the present disclosure for interlocking the second segment with the first segment.
Figure 3:
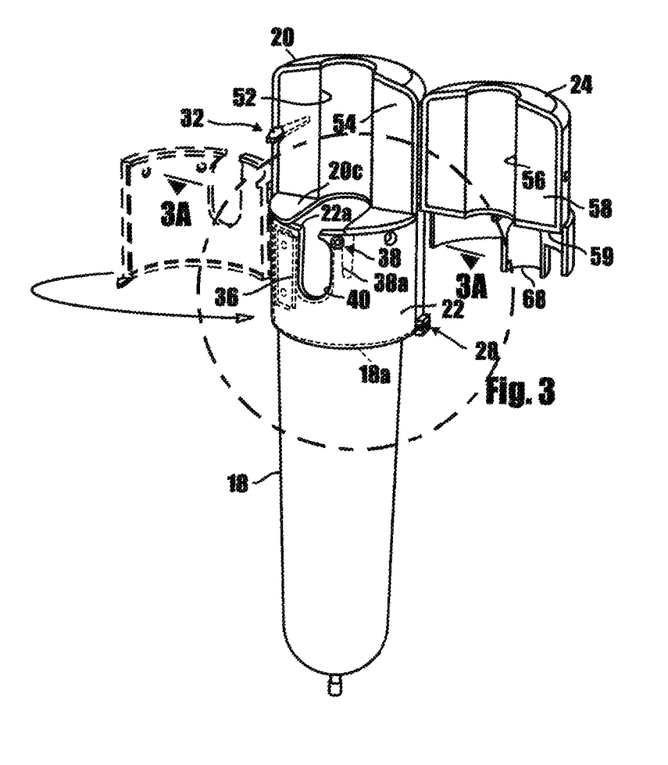
FIG. 3 is a front elevational view similar to FIG. 2, but showing the second segment of the retainer assembly of the cord collection clamp mated with the first segment of the retainer assembly.

As illustrated in FIG. 1, second segment 22 of the retaining assembly is connected to first segment 20 by a living hinge 26 and, in a manner presently to be described, is movable from a first position shown in FIG. 2 of the drawings to a second position shown in FIG. 3 wherein it overlays the upper portion 18a of the collection assembly 18 and interlocks with first segment 20 by means of an interlocking mechanism 28 of conventional design the character of which is illustrated in FIG. 2A of the drawings. As indicated in FIG. 3 interlocking mechanism 28 functions to interlock together first and second segments 20 and 22 when second segment 22 is in the second position.

Figure 4:
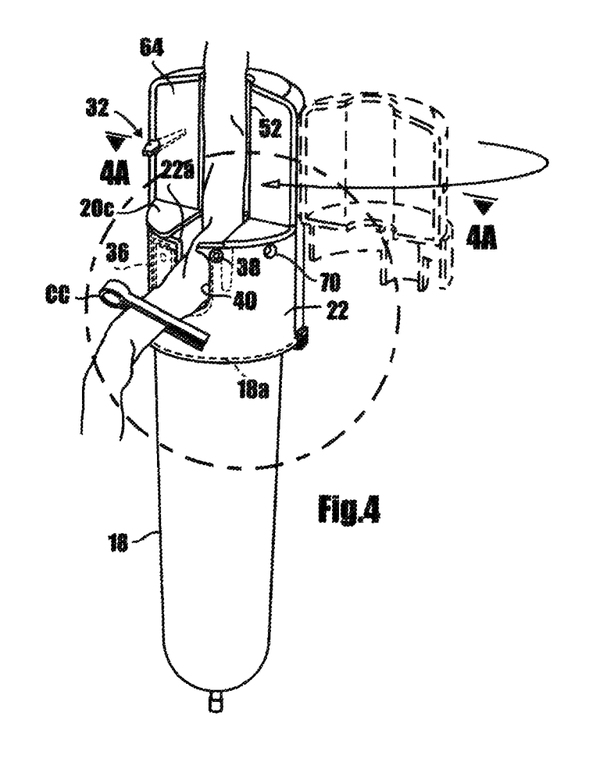
FIG. 4 is a front elevational view similar to FIG. 3, but showing the uncut umbilical cord entrained through the cord receiving channel of the retainer assembly of the device, showing the third segment of the retainer assembly of the cord collection clamp in dotted lines and illustrating the manner in which the third segment is rotated to mate with the first segment of the retainer assembly.
Figure 4A:
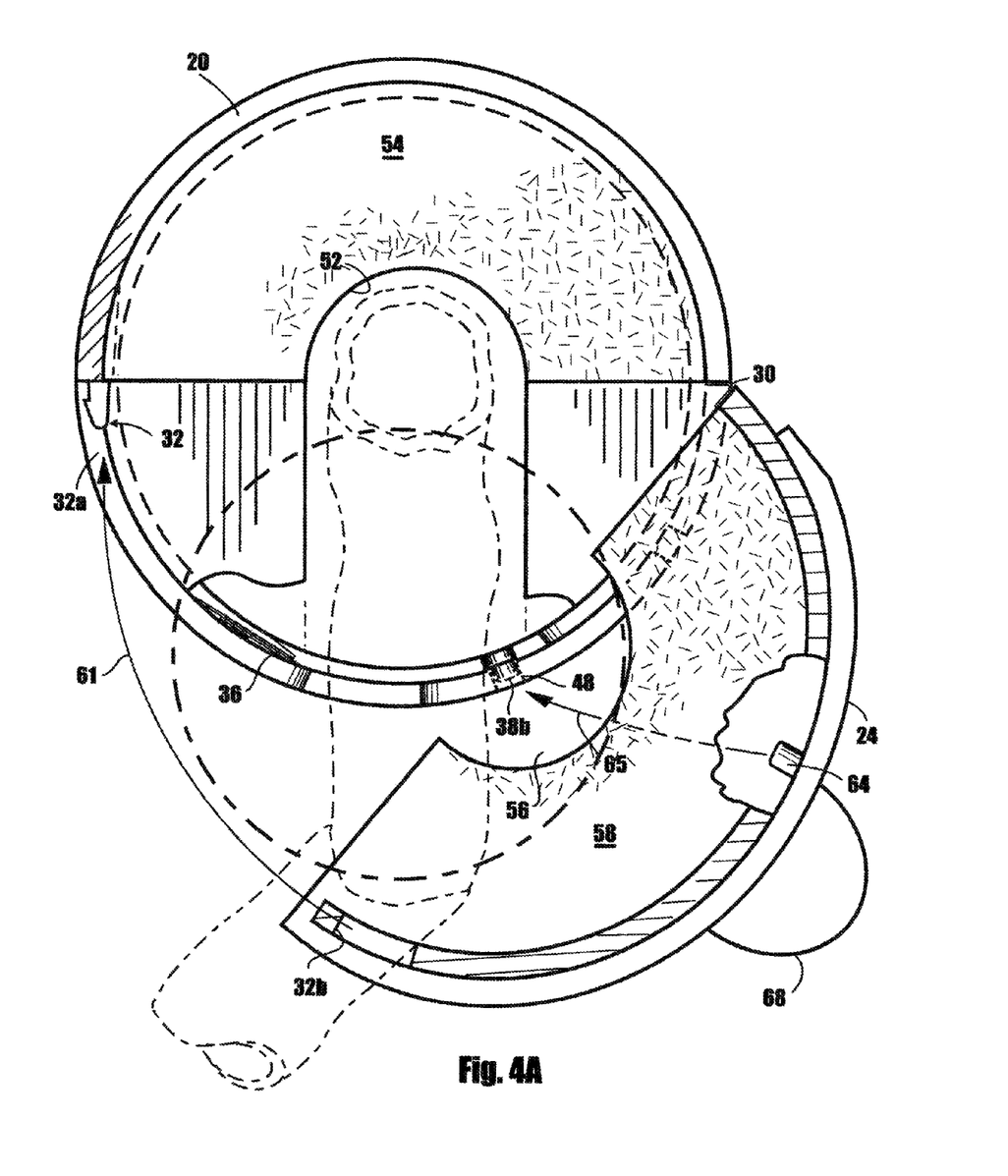
FIG. 4A is a cross-sectional view taken along lines 4A-4A of FIG. 4 illustrating the second segment of the retainer assembly interlocked with the first segment and showing the third segment of the retainer assembly moved toward a closed position.

Similarly, third segment 24 of the retaining assembly is connected to first segment 20 by a living hinge 30 and, in a manner presently to be described, is movable from a first position shown in FIG. 3 of the drawings to a second position shown in FIG. 5 wherein it overlays a portion of first segment 20 and interlocks with the first segment by means of a conventional locking mechanism 32 the character of which is illustrated in FIG. 4A of the drawings.

As best seen in FIG. 1, collection assembly 18 includes a collar 18b that is disposed intermediate upper portion 18a and lower catch reservoir portion 18c. The upper portion 18a of the collection assembly is provided with a generally U-shaped, umbilical cord receiving opening 34. Mounted proximate opening 34 is the important umbilical cord cutting blade 36 of the present disclosure. The upper portion 18a of the collection assembly also includes a locking assembly 38, which in a manner presently be described, functions to prevent accidental rotation of the collection assembly 18 relative to the retainer assembly 16.

It is to be noted that upon closing second segment 22, a generally U-shaped opening 40 formed in second segment 22 aligns with opening 34 formed in the collection assembly to permit passage of the umbilical cord. It is also important to note that upon closing second segment 22, the cutting edge of cutting blade 36 is covered by the blade covering protective portion 22a of second segment 22 (see FIG. 4). This important blade covering protective portion of the second segment, which is disposed proximate opening 40, functions to effectively protect the operator from being accidentally cut by the blade during the positioning of the umbilical cord within the cord collection clamp (see also FIGS. 2A and 3A).

Figure 3A:
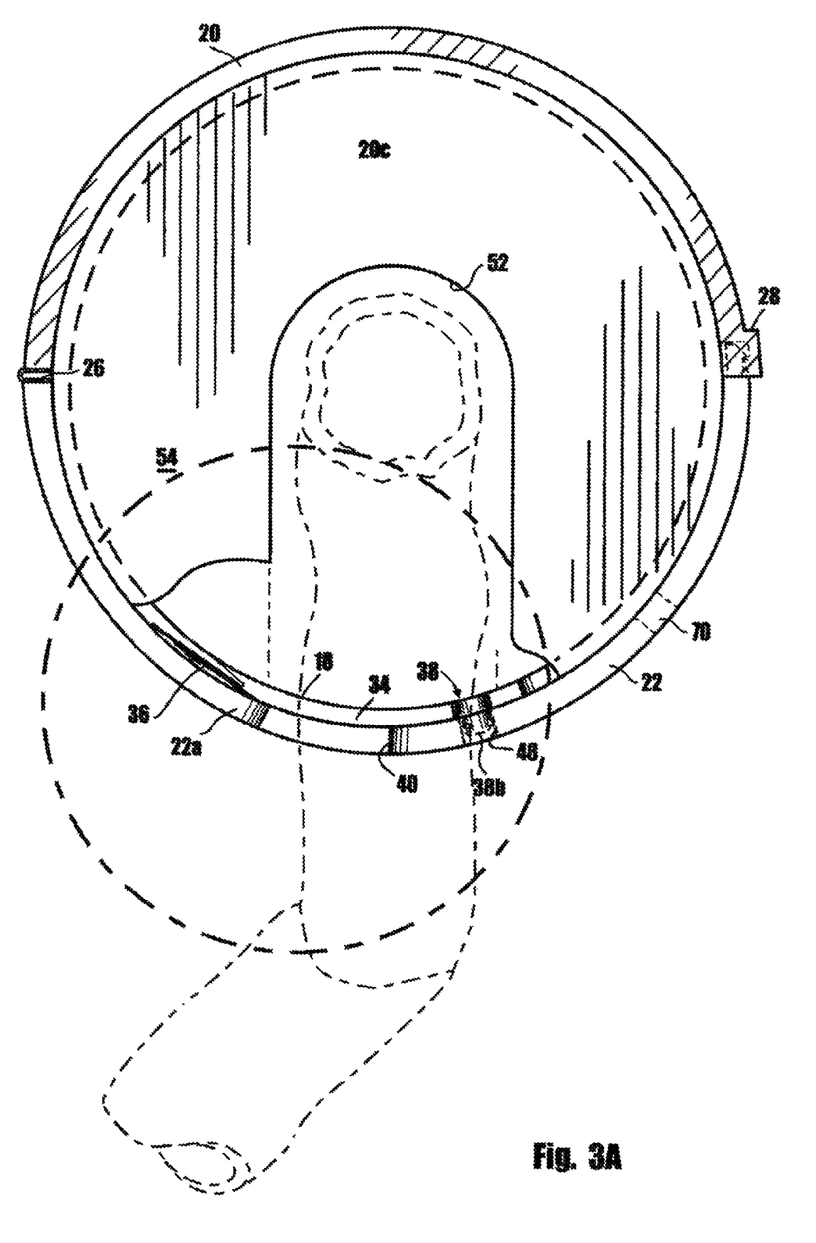
FIG. 3A is a cross-sectional view taken along lines 3A-3A of FIG. 3 illustrating the second segment of the retainer assembly interlocked with the first segment of the retainer assembly and also interlocked with the collection assembly so as to prevent rotation of the collection assembly relative to the retainer assembly.

As illustrated in FIG. 1 of the drawings, center segment 20 of the retainer assembly 16 is provided with an inwardly extending shoulder 42. Similarly, second segment 22 is provided with an inwardly extending shoulder 44 that mates with shoulder 42 when the second segment is moved into the closed position shown in FIG. 3 of the drawings. When the collection assembly 18 is mated with the retaining assembly in the manner shown in FIG. 2 of the drawings and when the second segment 22 is in the closed position, collar 18b the of the collection assembly engages shoulders 42 and 44 and functions as a removal preventing assembly that prevents removal of the collection assembly from the retainer assembly. Additionally, in a manner next to be discussed and as illustrated in FIGS. 2A and 3A of the drawings, when the second segment 22 is moved into the closed position, collection assembly 18 will be locked against rotation relative to the retainer assembly 16. This anti-rotation locking feature is accomplished by the previously identified locking assembly 38 which comprises a yieldably deformable locking finger 38a and a locking protuberance 38b that is formed proximate the extremity of the locking finger. As the second segment moves toward the closed position and as indicated by the arrow 45 in FIG. 2A, locking protuberance 38b will be received within a locking protuberance receiving aperture 48 formed in the second segment. With the locking protuberance positioned within locking protuberance receiving aperture 48 in the manner shown in FIG. 3A, the collection assembly 18 will be locked against rotation relative to the retainer assembly. Additionally, second segment 22 will be interlocked with segment 20 as the male portion 28a of interlocking mechanism 28 seats within female portion 28b.

Figure 4B:
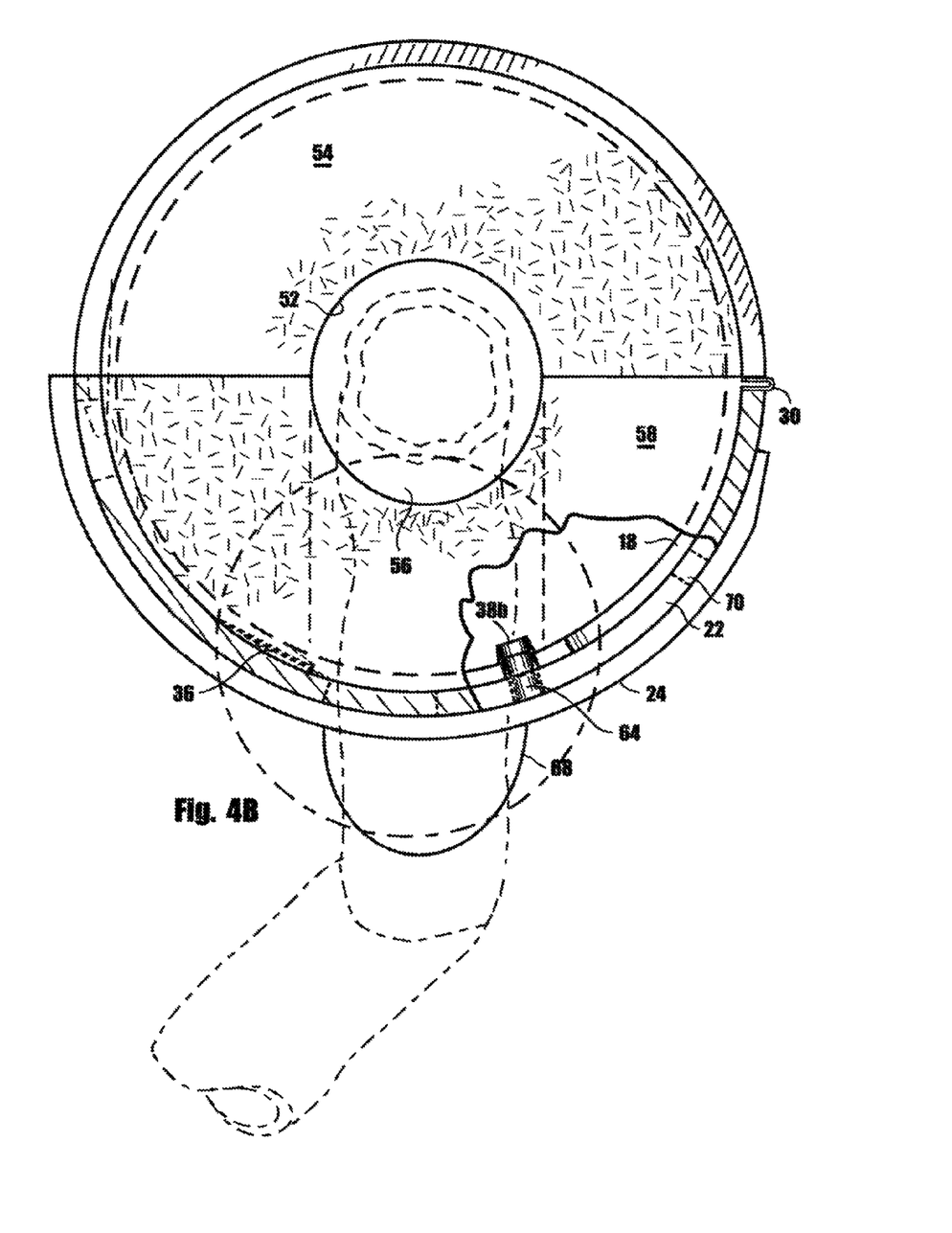
FIG. 4B is a cross-sectional view taken along lines 4B-4B of FIG. 6 showing the third segment of the retainer assembly moved into a closed position wherein it functions to act upon the locking protuberance of the collection assembly to permit rotation of the collection assembly relative to the retainer assembly.

With the cord collection clamp in the configuration illustrated in FIGS. 3 and 3A, wherein the collector assembly 18 is locked against removal from the retainer assembly, wherein a portion of the second segment 22 protectively covers the cutting blade 36 and wherein the collector assembly 18 is locked against rotation relative to the retainer assembly, the umbilical cord (shown by the dotted lines in FIG. 3A) can safely be positioned within the device in preparation of the cord cutting operation. With the conventional cord clamp CC in position so as to stop umbilical cord blood flow, the umbilical cord can be entrained through the online openings 34 and 40 in the manner illustrated in FIG. 4. As the umbilical cord is so positioned, the cord will be seated within a channel 52 that is formed within a foam insert 54 that is mounted in the upper portion of first segment 20. This done, the third segment 24 of the retainer assembly is moved from the position shown in the dotted lines in FIG. 4 into the closed position shown in FIG. 5. With the third segment in the closed position, the umbilical cord is closely received within a channel 56 that is formed within a foam insert 58 that is mounted in the upper portion of third segment 24. As illustrated in the drawings, foam insert 54 is supported within first segment 20 by the previously identified, inwardly extending wall 20c, while foam insert 58 is supported within third segment 24 by an intermediate, inwardly extending wall 59. It is to be appreciated that with the construction thus described, the generally U-shaped cord receiving openings 34 and 40 formed in the collection assembly and in the cord retaining assembly respectfully, cooperate with channels 52 and 56 to form the umbilical cord retaining channel of the present disclosure which functions to support the umbilical cord during the cutting operation. However, in this regard, it is to be appreciated that the umbilical cord cutting operation cannot be accomplished until the yieldably deformable locking finger of the locking assembly 38 is acted upon by the release assembly of the present disclosure in a manner to permit rotation of the collection assembly relative to the cord retaining assembly. It is to be appreciated that movement of the third segment of the retainer assembly into the closed position shown in FIG. 5 not only clamps the umbilical cord in position, but also actuates the release assembly of the present disclosure in a manner next to be described. More particularly, as illustrated in FIGS. 4A and 4B of the drawings, as the third segment 24 moves into the closed position as indicated by the arrow 61 in FIG. 4A, a release protuberance 64 provided on the inner wall of third segment, which forms a part of the release assembly of the present disclosure, moves toward protuberance 38b of assembly 38 in the direction of the arrow 65. When the third segment 24 reaches the closed position shown in FIG. 4B, the yieldably deformable locking finger along with protuberance 38b will have been moved inwardly by protuberance 64 and clear of aperture 48 formed in second segment 22 so as to no longer block rotation of the collection assembly. Additionally, third segment 24 will be interlocked with segment 20 as the locking tab 32a of interlocking mechanism 32 seats within tab receiving portion 32b. With the third segment 24 in the closed position, a protective sleeve 68 formed on third segment 24 covers the generally U-shaped opening 40 that forms a part of the umbilical cord channel and thereby functions to further protect the operator from accidental cutting by the cutting blade.

Figure 6:
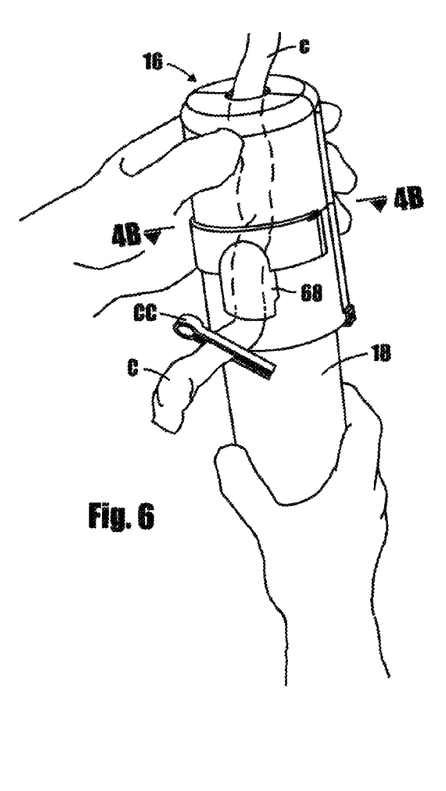
FIG. 6 is a diagrammatic view similar to FIG. 5 showing the manner in which the retainer assembly is gripped by the user and the manner in which the collection assembly is gripped by the user prior to rotation of the collection assembly.
Figure 7:
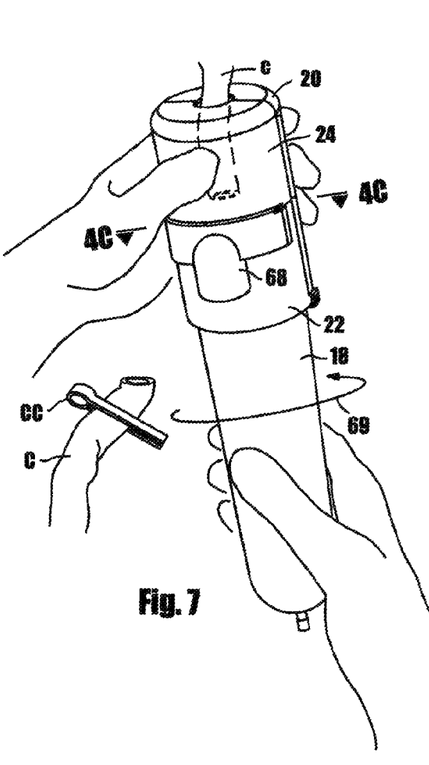
FIG. 7 is a diagrammatic view similar to FIG. 6, but illustrating the manner in which the collection assembly is rotated relative to the retainer assembly to sever the umbilical cord.

As illustrated in FIGS. 6 and 7 of the drawings, in accomplishing the severing operation, the retainer assembly is gripped with one hand of the user and the collection assembly is gripped by the other hand so that the collection assembly can be rotated in the manner indicated by the arrow 69 of FIG. 7. As the collection assembly is rotated, the cutting blade will traverse the portion of the cord retaining channel defined by the cord receiving openings 34 and 40 thereby severing the umbilical cord. More particularly, as illustrated in FIGS. 4B and 4C, as the collection assembly is rotated, the cutting blade 36 will traverse the cord receiving opening 34 in said second segment of the retainer assembly thereby cleanly severing the umbilical cord in the manner shown in FIG. 4C.

Figure 4C:
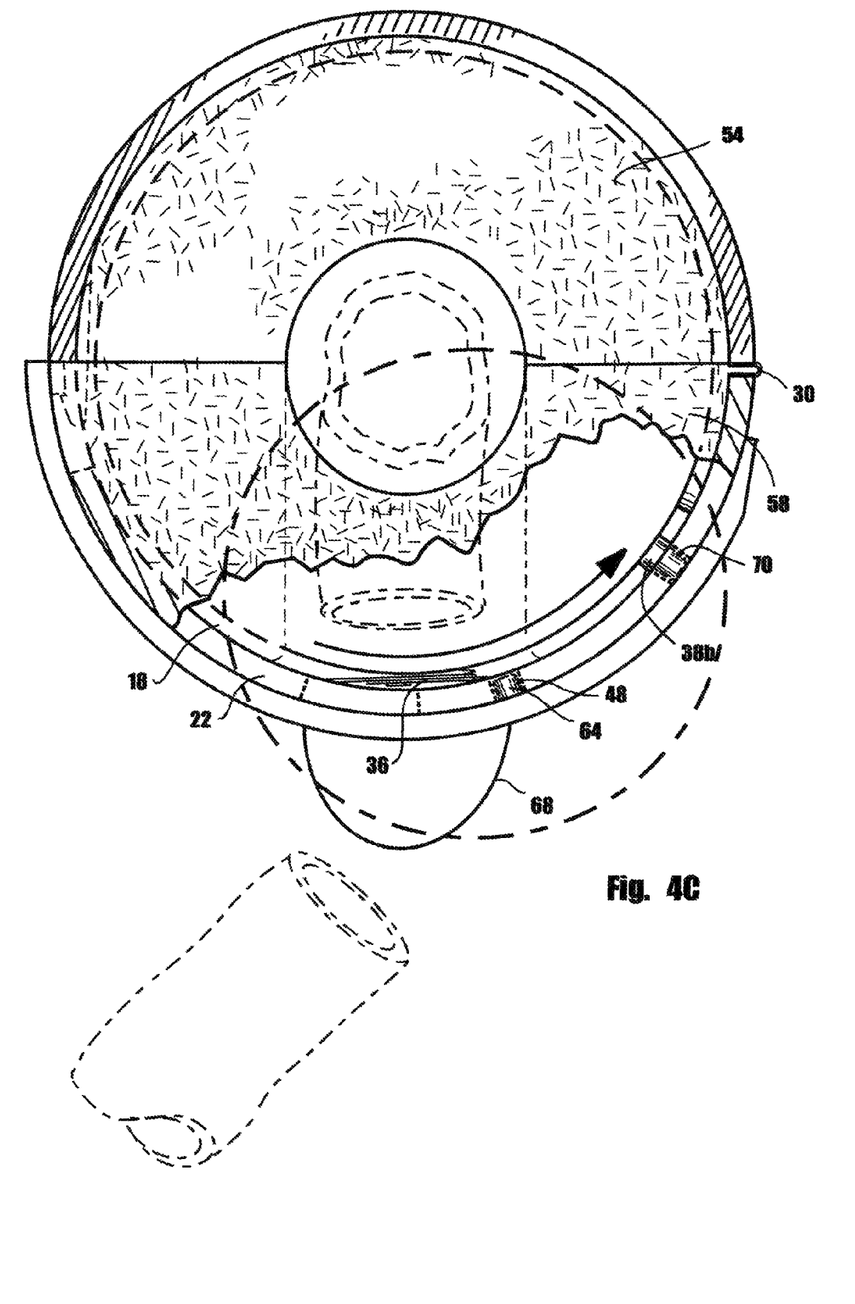
FIG. 4C is a cross-sectional view taken along lines 4C-4C of FIG. 7 illustrating the rotation of the collector assembly of the present disclosure relative to the retainer assembly in a manner to cleanly cut the umbilical cord and also showing the relocking of the collector assembly against rotation relative to the retainer assembly to thereby disable the device from opening.

Referring particularly to FIG. 4C of the drawings, it is to be noted that as the collection assembly 18 is rotated in the direction of the arrow of FIG. 4C, the outwardly extending protuberance 38b formed on the deformable locking finger 38a will move into alignment with a disabling aperture 70, which forms a part of the disabling assembly of the present disclosure, and will be lockably received there within thereby disabling the cord collection clamp and preventing further rotation of the collection assembly relative to the retaining assembly.

After the umbilical cord is severed, blood will flow from the cord via gravity into the blood collection region 18c of the collection assembly. Since the blood collection assembly is at this point substantially closed to the external environment, the blood is therefore collected in a substantially aseptic environment. In practice, the lower portion of the blood collection assembly acts as a funnel to funnel the blood toward an outlet port 18p to which an external collection bag (not shown) can be interconnected.

Having now described the present disclosure in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the present disclosure as set forth in the following claims.

I claim:
1. A cord collection clamp for collecting blood from an umbilical cord comprising:
  (a) a retainer assembly having an umbilical cord channel constructed and arranged to allow the umbilical cord to pass therethrough, said retainer assembly having an outlet in communication with said umbilical cord channel, wherein said retainer assembly comprises:

(i) a first segment;
(ii) a second segment hingeably connected to said first segment and movable from a first position to a second position; and
(iii) a third segment hingeably interconnected to said second segment and movable from a first position to a second position; and
(b) a blood collection assembly rotatably connected to said retainer assembly, said blood collection assembly having an inlet in communication with said outlet of said retainer assembly,
wherein said second position of said second segment overlays a portion of said blood collection assembly, and said second position of said third segment overlays a portion of said first segment and overlays a portion of said blood collection assembly;
wherein said blood collection assembly of said cord collection clamp comprises a locking protuberance for blocking rotation of said retainer assembly relative to said blood collection assembly and in which said second segment of said retainer assembly is provided with an aperture arranged to receive said locking protuberance when said second segment is in said second position of said second segment;
wherein said third segment of said retaining assembly comprises a release protuberance constructed and arranged to act upon said locking protuberance of said blood collection assembly to remove said locking protuberance from said aperture of said second segment of said retainer assembly when said third segment is in said second position of said third segment; and
said blood collection assembly comprising a cord cutting blade constructed and arranged to traverse said umbilical cord channel upon rotation of said blood collection assembly relative to said retainer assembly, thereby cutting the umbilical cord.

2. The cord collection clamp as defined in claim 1, wherein said second segment comprises a cord cutting blade covering portion arranged to cover said cord cutting blade when said second segment is in said second position of said second segment.

3. The cord collection clamp as defined in claim 1 in which said retainer assembly further comprises a foam insert constructed and arranged to circumscribe a portion of the umbilical cord.

4. The cord collection clamp as defined in claim 1 in which said third segment comprises a protective sleeve constructed and arranged to cover said umbilical cord channel when said third segment is in said second position of said third segment.

5. A cord collection clamp for collecting blood from an umbilical cord comprising:
(a) a retainer assembly comprising a first segment, a second segment hingeably connected to said first segment, said second segment having a cord receiving opening and being movable from a first position to a second position, and a third segment hingeably interconnected to said second segment, said third segment being movable from a first position to a second position and comprising a protective sleeve constructed and arranged to cover said cord receiving opening in said second segment of said retainer assembly when said third segment is in said second position of said third segment; and
(b) a blood collection assembly rotatably connected to said retainer assembly, said second position of said third segment overlaying a portion of said first segment and overlaying a portion of said blood collection assembly, and said blood collection assembly having a cord receiving opening and a cord cutting blade constructed and arranged to traverse said cord receiving opening in said second segment of said retainer assembly upon rotation of said blood collection assembly relative to said retainer assembly.

6. The cord collection clamp as defined in claim 5 in which said second segment of said retainer assembly further comprises a protective covering portion arranged to cover said cord cutting blade when said second segment is in said second position of said second segment.

7. The cord collection clamp as defined in claim 5 in which said second segment further comprises a locking protuberance for blocking rotation of said blood collection assembly relative to said retainer assembly when said segment is in said second position of said second segment.

8. The cord collection clamp as defined in claim 7 in which said third segment of said retaining assembly comprises a release protuberance constructed and arranged to act upon said locking protuberance of said blood collection assembly to permit rotation of said blood collection assembly relative to said retainer assembly when said third segment is in said second position of said third segment.

9. The cord collection clamp as defined in claim 8 in which said second segment of said retaining assembly includes a disabling aperture arranged to receive said locking protuberance of said blood collection assembly upon rotation of said blood collection assembly relative to said retainer assembly to block rotation of said blood collection assembly.

10. A cord collection clamp for collecting blood from an umbilical cord comprising:
(a) a retainer assembly comprising:
(i) a first segment;
(ii) a second segment hingeably connected to said first segment, said second segment having a cord receiving opening and being movable from a first position to a second position; and
(iii) a third segment hingeably interconnected to said second segment and movable from a first position to a second position; and
(b) a blood collection assembly rotatably connected to said retainer assembly, said blood collection assembly having a cord receiving opening and a cord cutting blade constructed and arranged to traverse said cord receiving opening in said second segment of said retainer assembly upon rotation of said blood collection assembly relative to said retainer assembly,
wherein said second segment of said retainer assembly comprises a protective covering portion arranged to cover said cord cutting blade when said second segment is in said second position of said second segment and further comprises a locking protuberance for blocking rotation of said blood collection assembly relative to said retainer assembly when said second segment is in said second position of said second segment, and
wherein said second position of said third segment overlays a portion of said first segment and overlays a portion of said blood collection assembly and wherein said third segment of said retainer assembly comprises a release protuberance constructed and arranged to act upon said locking protuberance of said blood collection assembly to permit rotation of said blood collection assembly relative to said retainer assembly when said third segment is in said second position of said third segment.

11. The cord collection clamp as defined in claim 10 in which said second segment of said retaining assembly comprises a disabling aperture arranged to receive said locking protuberance upon rotation of said blood collection assembly relative to said retainer assembly to block rotation of said blood collection assembly.

12. A method of collecting cord blood, the method comprising:
   positioning an umbilical cord in the umbilical cord channel of the retainer assembly of the cord collection clamp of claim 1;
   rotating the retainer assembly relative to the blood collection assembly thereby clamping the umbilical cord into position and actuating the cutting blade to cut the umbilical cord.

13. A method of collecting cord blood, the method comprising:
   positioning an umbilical cord in the cord receiving opening of the retainer assembly of the cord collection clamp of claim 5;
   rotating the retainer assembly relative to the blood collection assembly thereby clamping the umbilical cord into position and actuating the cutting blade to cut the umbilical cord.

14. A method of collecting cord blood, the method comprising:
   positioning an umbilical cord in the cord receiving opening of the retainer assembly of the cord collection clamp of claim 10;
   rotating the retainer assembly relative to the blood collection assembly thereby clamping the umbilical cord into position and actuating the cutting blade to cut the umbilical cord.

* * * * *